United States Patent [19]

Mustakallio

[11] Patent Number: 5,021,185

[45] Date of Patent: Jun. 4, 1991

[54] CLEANSING-AGENT COMPOSITION AND ITS USE

[75] Inventor: Kimmo K. Mustakallio, Helsinki, Finland

[73] Assignee: Orion-Yhtma Oy, Finland

[21] Appl. No.: 378,370

[22] Filed: Jul. 11, 1989

[30] Foreign Application Priority Data

Jul. 12, 1988 [FI] Finland ................................. 883310

[51] Int. Cl.$^5$ ........................... C11D 1/12; C11D 7/08
[52] U.S. Cl. ..................................... 252/142; 252/550; 252/554; 252/DIG. 5
[58] Field of Search ............... 252/136, 142, 550, 554, 252/DIG. 5; 424/659; 514/863

[56] References Cited

U.S. PATENT DOCUMENTS

| | | | |
|---|---|---|---|
| 4,321,156 | 3/1982 | Bushman | 252/136 |
| 4,454,118 | 6/1984 | Johnson | 424/659 |
| 4,485,027 | 11/1984 | Rossman | 252/136 |
| 4,495,079 | 1/1985 | Good | 252/DIG. 5 |
| 4,612,193 | 9/1986 | Gordon | 424/659 |
| 4,816,254 | 3/1989 | Moss | 424/145 |

FOREIGN PATENT DOCUMENTS

| | | |
|---|---|---|
| 357681 | 2/1978 | Australia . |
| 1479543 | 7/1977 | United Kingdom . |
| 1480314 | 7/1977 | United Kingdom . |
| 1513053 | 6/1978 | United Kingdom . |

OTHER PUBLICATIONS

Lane, "Spectrofluorometric Method for the Determination of Hydroxylated Anthracene Derivatives and its Application to the Assay of Senna Derivatives in Biological Tissues," Anal. Chem., vol. 45, No. 11, pp. 1911–1914, Sep. 1973.

Mustakallio et al., "Determination of Dithranol (Anthralin) as a Fluorescent Borate Complex", Psoriasis Proceedings of the Third International Symposium at Stanford University, pp. 375–376 (1981).

Primary Examiner—Josephine Barr
Assistant Examiner—Alexander G. Ghyka
Attorney, Agent, or Firm—Brumbaugh, Graves, Donohue & Raymond

[57] ABSTRACT

There is disclosed a cleansing-agent which is particularly useful for the removal from the skin or other surfaces of substances, such as dithranol, which form water-soluble complexes with boric acid. The cleansing-agent comprises by weight (a) boric acid, 1–3%; (b) anionic detergent, 0.5–20%; (c) fatty alcohol, 5–30%; and (d) fatty vehicle comprising at least ethoxylated glycerides of saturated fatty acids, 30–75%, and may also include as a fatty vehicle a glyceride of unsaturated and/or saturated fatty acid.

31 Claims, No Drawings

CLEANSING-AGENT COMPOSITION AND ITS USE

BACKGROUND OF THE INVENTION

The invention relates to a cleansing-agent composition containing boric acid, and its use for cleansing the skin, clothing and fixtures from substances which form water-soluble complexes with boric acid, and specifically for removing from the skin the surplus of dithranol in the treatment of psoriasis.

One of the preparations most commonly used for the treatment of psoriasis is dithranol. Dithranol does not cause permanent or severe side effects, as do cortisone derivatives, but its use has been limited by skin irritation cause by its oxidation via radicals, as well as by the coloration of the skin and clothing. In recent years it has been possible to reduce these drawbacks by using dithranol in stick form, as disclosed in Patent FI 66533, in which case the treatment can be focussed mainly on plaques of eczema, or as so-called minute therapy, short-contact therapy, in which the excess of dithranol is removed from the skin 10–20 minutes after the application (Runne et al., Hautarzt 1985:36 40–46). The removal of the dithranol surplus requires absorption of the therapeutic ointment in a soft paper towel, for example by patting the treated areas with a paper towel, and additionally washing with acidic or neural washing liquids which do not accelerate the oxidation of dithranol into colored compounds. In order to avoid the staining of the skin, clothing and bathroom fixtures, as well as the irritation of the skin, in short-contact dithranol therapy, it must be possible to remove the surplus dithranol rapidly and as completely as possible. The removal of dithranol by mere washing is difficult, since dithranol and its dark oxidation products are practically water-insoluble and adhere to the skin as well as to fibers and bathroom fixtures. In addition, dithranol preparations are based on water-immiscible fatty vehicles, such as petrolatum and paraffins, 1) since dithranol dissolves in petrolatum and paraffins better than in other ointment bases, 2) since dithranol is more stable in them than in water-containing ointment bases, and 3) since dithranol is taken up by the skin better from them than from water-containing or hydrophilic ointment bases.

So far, boric acid has been used in various skin cleansers mainly as a buffer or as a disinfectant, as in Patent FR 2480120. Alkali borates and borax have been used in skin cleansing preparations as scouring agents in order to increase the cleansing effect (FR 2172803 and DE 2033016) or in order to provide a protective ointment layer on the skin (FR 2231397). However, the ability of boric acid to form water-soluble complexes (chelates) with certain water-insoluble substances, specifically with dihydrodiols which contain cyclic hydrocarbons, has so far not been exploited in skin cleansing agents.

In order to eliminate the above problems encountered in dithranol treatment, a new washing ointment composition has been developed. The constituents of the washing ointment according to the invention facilitate the emulsification of the fatty vehicles of dithranol preparations and the conversion of dithranol into a water-soluble borate chelate, which ensures the rapid and complete removal from the skin of any dithranol surplus remaining in the horny layer and the surface of the skin. This for its part prevents the coloration of the skin, clothing and bathroom fixtures, and reduces skin irritation. At the same time, the invention renders unnecessary the patting of the skin with paper towels before washing and the use of simple creams after the wash. The invention is also suitable for washing, immediately after staining, any fibers and surfaces stained by dithranol preparations. Furthermore, the invention can also be used for removing from the skin surfaces, for example in an industrial environment, other substances which form chelates with boric acid.

The constituents of the composition according to the invention constitute an optimal composition for converting dithranol into water-soluble borate chelate in mildly acid or almost neutral conditions. At the same time the anionic detergent and fats present in the ointment facilitate the emulsification of both petrolatum and paraffins and more hydrophilic ointment bases into washable micelles. Borate ions capture into the aqueous phase the dithranol molecules which have ended up on the surface of the micelles because of their hydroxyl groups. In the washing water the water-soluble borate chelates of dithranol remain without breaking down to dithranol at least for the duration of the washing, and so dithranol washes off the skin and leaves the washing bowl in a water-soluble form and does not cause coloration of the fixtures.

The borate chelate of dithranol is strongly greenish yellow fluorescent in UV light, and the fluorescence disappears as soon as the dithranol is broken down from the chelate form (Mustakallio et al., Psoriasis: Proceedings of the Third International Symposium, Stanford University 1981, pp. 375–376). This fluorescence phenomenon can be exploited in measuring the rapidness and completeness of the washing off of the dithranol surplus and the stability of the water-soluble dithranol borate chelate in the washing water. When a paraffin-, petrolatum-, or emulsion-based dithranol preparation is used in short-contact therapy and the washing ointment according to the invention is used for the wash in an amount approximately double that of the dithranol preparation, the surplus dithranol can be removed by one posttreatment wash in some twenty seconds, judging from the fluorescence of the skin and of the washing water and from the fact that a repeat application of the ointment does not cause fluorescence in fresh washing water.

Owing to the protective and anti-drying fats present in it, the composition according to the invention does not cause drying or additional irritation of the skin even during a month's period of daily treatment. On the other hand, when conventional acidic or neutral cleansing liquids are used in connection with short contact dithranol therapy, it is in general necessary to use some simple cream to reduce the drying and irritation of the skin. The ointment-like properties of the composition according to the invention is also suitable for the washing of textiles and plastics as well as ceramic and enamel surfaces stained by dithranol preparations, if the washing is carried out before the dithranol has oxidized into dark compounds, which is accelerated by alkaline conditions.

The composition according to the invention comprises the following constituents, the concentration limits (in percent by weight) and functioning principles of which are described below:

(1) Boric acid (1–3%) is an essential constituent of the invention, and together with a water-containing anionic detergent (2) it provides a possibility of the formation of borate ions in almost neutral conditions, in which case the rate of formation and stability of the water-soluble dithranol borate chelate are optimal for the washing purpose.

(2) An anionic detergent (0.5–20%), preferably (10–15%), for example sodium lauryl ether sulfate (70%), together with a fatty alcohol (3) is that constituent of the invention which emulsifies petrolatum and paraffins into micelles and at the same time yields sodium ions to boric acid, promoting, by buffering, the formation of dithranol borate chelate.

(3) A fatty alcohol (5–30%), preferably (20–25%), for example cetostearyl alcohol, together with an anionic detergent (2) is that constituent of the invention (emulsifying wax for washable ointments) which emulsifies even petrolatum and paraffins into micelles to be carried away by a washing-water flow.

(4) A fatty vehicle (30–75%), comprises glycerides of saturated fatty acids, rendered water-soluble by ethoxylation (e.g. PEG-6 Caprylic/Capric Glyceride) and optionally glycerides of unsaturated and/or saturated fatty acids (for example ricinoleic acid glyceride). The fatty vehicles protect the skin from irritation, prevent the skin from drying, and accelerate the normalization of its fat content after the wash. They are also more easily emulsifiable than paraffins and petrolatum, the emulsification of which they promote. If the fatty vehicle has a mono-di-glyceride structure, it also has emulsion-stabilizing action. The glyceride of a fatty acid which contains free hydroxyl groups (such as ricinoleic acid) binds dithranol to some extent via hydrogen bridges.

The invention is illustrated with the following examples without, however, restricting the invention to them:

EXAMPLE 1

| | |
|---|---|
| Boric acid | 1.0 |
| Sodium lauryl ether sulfate (70%) | 10.0 |
| Cetostrearyl alcohol | 22.0 |
| Ricinoleic acid glyceride (Softigen 701) | 5.0 |
| PEG-6 Caprylic/Capric Glyceride (Softigen 767) | 61.0 |

The washing ointment according to Example 1 is suitable for long-term use, since the glyceride of ricinoleic acid renders it gentle on the skin.

EXAMPLE 2

| | |
|---|---|
| Boric acid | 3.0 |
| Sodium lauryl ether sulfate (70%) | 15.0 |
| Cetostearyl alcohol | 25.0 |
| PEG-6 Caprylic/Capric Glyceride (Softigen 767) | 57.0 |

The washing ointment according to Example 2 has a stronger washing action and is best suited for removing the surplus dithranol when preparations having a high dithranol content are used.

| | |
|---|---|
| Boric acid | 2.0 |
| Sodium lauryl ether sulfate (70%) | 10.0 |
| Cetostearyl alcohol | 20.0 |
| Ricinoleic acid glyceride (Softigen 701) | 5.0 |
| Glycerol | 5.0 |
| PEG-6 Caprylic/Capric Glyceride (Softigen 767) | 58.0 |

The outer appearance and convenience in use of the washing ointment according to Example 3 are good.

I claim:
1. A cleansing-agent composition, comprising the following constituents by weight:
   (a) boric acid, 1–3%;
   (b) anionic detergent, 0.5–20%;
   (c) fatty alcohol, 5–30%; and
   (d) fatty vehicle comprising at least ethoxylated glycerides of saturated fatty acids, 30–75%,
said composition having the ability to form a borate chelate with a dihydrodiol which contains cyclic hydrocarbon.

2. A composition according to claim 1, wherein the anionic detergent comprises 10–15% of the weight of the composition.

3. A composition according to claim 1, wherein the fatty alcohol comprises 20–25% of the weight of the composition.

4. A composition according to claim 1, wherein the anionic detergent is comprised of 70% sodium lauryl ether sulfate.

5. A composition according to claim 1, wherein the fatty alcohol/detergent combination is an emulsifying wax for washable ointments.

6. A composition according to claim 1, wherein the fatty alcohol is comprised of cetostearyl alcohol.

7. A composition according to claim 1, wherein the fatty vehicle is also comprised of a glyceride of unsaturated and/or saturated fatty acid.

8. A composition according to claim 7, wherein the fatty vehicle also comprises an unsaturated fatty acid ester which contains free hydroxyl groups.

9. A composition according to claim 1, wherein the fatty vehicle comprises a fatty acid mono-di-glyceride.

10. A composition according to claim 7, wherein the fatty vehicle comprises ricinoleic acid glyceride.

11. A composition according to claim 1, wherein the fatty vehicle comprises an ethoxylated glyceride of natural saturated vegetable fatty acids.

12. A composition according to claim 1, wherein the fatty vehicle comprises PEG-6 Caprylic/Capric Glyceride.

13. A method of removing a substance from a surface or fabric, wherein said substance contains a dihydrodial which contains cyclic hydrocarbons and which forms water-soluble chelates with boric acid, said method comprising the steps of applying to said surface or fabric a cleansing-agent composition so as to form a chelate with said dihydrodiol, and thereafter rinsing the cleansing agent and chelate from said surface or fabric, said cleansing agent comprising the following constitutents by weight:
   (a) boric acid, 1–3%;
   (b) anionic detergent, 0.5–20%;
   (c) fatty alcohol, 5–30%; and
   (d) fatty vehicle comprising at least ethoxylated glycerides of saturated fatty acids, 30–75%.

14. A method according to claim 13, wherein the substance forming water-soluble chelates with boric acid is dithranol.

15. A method according to claim 13, wherein the surface is the skin of a psoriatic, and wherein the cleansing agent is rinsed from the skin without staining the skin.

16. A method according to claim 13, wherein the surface is a plumbing fixture and stain from dithranol is removed from said fixture by the application of the cleansing agent and rinsing.

17. A method according to claim 13, wherein stain from dithranol is removed from fabric by the application of the cleansing agent and rinsing.

18. A method according to claim 13, wherein the anionic detergent comprises 10-15% of the weight of the composition.

19. A method according to claim 13, wherein the fatty alcohol comprises 20-25% of the weight of the composition.

20. A method according to claim 13, wherein the anionic detergent is comprised of 70% sodium lauryl ether sulfate.

21. A method according to claim 13, wherein the fatty alcohol/detergent combination is an emulsifying wax for washable ointments.

22. A method according to claim 13, wherein the fatty alcohol is comprised of cetostearyl alcohol.

23. A method according to claim 13, wherein the fatty vehicle is also comprised of a glyceride of unsaturated and/or saturated fatty acid.

24. A method according to claim 13, wherein the fatty vehicle also comprises an unsaturated fatty acid ester which contains free hydroxyl groups.

25. A method according to claim 13, wherein the fatty vehicle comprises a fatty acid mono-di-glyceride.

26. A method according to claim 13, wherein the fatty vehicle comprises ricinoleic acid glyceride.

27. A method according to claim 13, wherein the fatty vehicle comprises an ethoxylated glyceride of natural saturated vegetable fatty acids.

28. A method according to claim 13, wherein the fatty vehicle comprises PEG-6 Caprylic/Capric Glyceride.

29. A composition according to claim 1, comprising the following constituents by weight:
 (a) boric acid, 1-3%;
 (b) sodium lauryl ether sulfate (70%), 10-15%;
 (c) cetostearyl alcohol, 20-25%; and
 (d) PEG-6 Caprylic/Capric Glyceride, 50-65%.

30. A composition according to claim 1, comprising the following constituents by weight:
 (a) boric acid, 1-3%;
 (b) sodium lauryl ether sulfate (70%), 10-15%;
 (c) cetostearyl alcohol, 20-25%;
 (d) ricinoleic acid glyceride, 5-10%; and
 (e) PEG-6 Caprylic/Capric Glyceride, 50-65%.

31. A composition according to claim 1, wherein said dihydrodiol is dithranol.

* * * * *